(12) United States Patent  (10) Patent No.: US 7,470,820 B2
Knopff et al.  (45) Date of Patent: Dec. 30, 2008

(54) SUBSTITUTED CYCLOHEXANONES

(75) Inventors: Oliver Knopff, Geneva (CH); Charles Fehr, Versoix (CH); José Galindo, Grand-Saconnex (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/916,258

(22) PCT Filed: Jul. 18, 2006

(86) PCT No.: PCT/IB2006/052460

§ 371 (c)(1),
(2), (4) Date: Nov. 30, 2007

(87) PCT Pub. No.: WO2007/010483

PCT Pub. Date: Jan. 25, 2007

(65) Prior Publication Data

US 2008/0228008 A1 Sep. 18, 2008

(30) Foreign Application Priority Data

Jul. 19, 2005 (EP) .................. 05106582

(51) Int. Cl.
*C07C 49/303* (2006.01)
*C07C 45/65* (2006.01)
(52) U.S. Cl. ..................... 568/343; 568/376
(58) Field of Classification Search .............. 568/343, 568/376
See application file for complete search history.

(56) References Cited

U.S. PATENT DOCUMENTS

2006/0252967 A1 11/2006 Knopff .............. 568/341

FOREIGN PATENT DOCUMENTS

WO 2005/077875 A1 8/2005

OTHER PUBLICATIONS

International Search Report and Written Opinion for PCT/IB2006/052460.
Charles Fehr et al., XP002365012, "An Efficient Enantioselective Synthesis Of (+)-(R,Z)-5-Muscenone and (−)-(R)-Muscone—An Example of a Kinetic Resolution and Enantioconvergent Transformation", Eur. J. Org. Chem.,pp. 1953-1957 (2004).
Claude Agami et al., XP002285952, "Enantioselective Cyclizations Of Acyclic 1,5-Diketones" Bulletin De La Societe Chimique De France, No. 2, pp. 358-360 (1987).
Barry B. Snider et al., XP002365013, "Lewis acid Catalyzed Ene Reactions of alpha, Beta-Unsaturated N-Acyloxazolidinones", J. Org. Chem., vol. 56, pp. 4908-4913, (1991).

*Primary Examiner*—Sikarl A Witherspoon
(74) *Attorney, Agent, or Firm*—Winston & Strawn LLP

(57) ABSTRACT

The present invention relates to a cyclohexanone derivative of formula

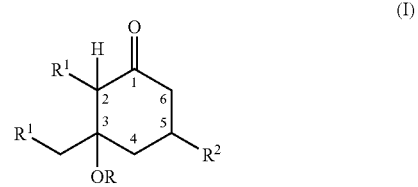

in the form of any one of its isomers or mixture thereof. The invention concerns also the preparation and the use of this derivative. The compounds of the invention are useful starting materials for the preparation of various optically active compounds.

12 Claims, No Drawings

SUBSTITUTED CYCLOHEXANONES

TECHNICAL FIELD

The present invention relates to the field of organic synthesis and more specifically it concerns a cyclohexanone derivative of formula

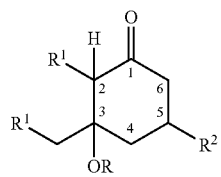

(I)

in the form of any one of its isomers or mixture thereof and as defined below. The invention concerns also the preparation and the use, as starting material, of said derivative.

PRIOR ART

To the best of our knowledge, the cyclohexanone derivatives of formula (I) are new compounds. Furthermore, in the prior art we have not found any method allowing the preparation of an analogue of the invention's cyclohexanones, i.e. compounds that have a hydroxy derivative in position 3 and a hydrocarbon derivative in position 5.

The cyclohexanone derivatives of formula (I) are useful starting materials to prepare the corresponding cyclohexenone. In WO 05/077875 the inventor describes a method to prepare similar cyclohexenones, however this prior art method requires the use of dione instead of the compound of formula (I).

Snider et al. (J. Org. Chem., 1991, 4908), Agami et al. (Bull. Soc. Chim. Fr., 1987, 358) or Fehr et al. (Eur. J. Org. Chem., 2004, 1953) describe also alternative methods to prepare similar cyclohexenones, however these methods imply the use of different starting materials as well as of different reagents.

DESCRIPTION OF THE INVENTION

We have now found a new class of cyclohexanones which are useful intermediates for the preparation of various compounds which can have specific configurations or are optically active.

Therefore, a first object of the present invention is a compound of formula

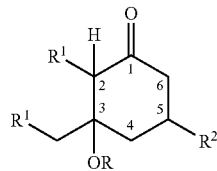

(I)

wherein the $R^1$, taken separately, are identical and represent an achiral $C_{1-10}$ linear, branched or cyclic alkyl or alkenyl group optionally substituted, or alternatively said two $R^1$, taken together, represent a linear $C_3$-$C_{10}$ alkanediyl or alkenediyl group optionally substituted;

$R^2$ represents an achiral $C_{1-7}$ linear, branched or cyclic alkyl or alkenyl group optionally substituted or a phenyl or benzyl group optionally substituted; and R represents:
  a hydrogen atom,
  a group of formula $Si(R^3)_3$, $R^3$ representing a $C_{1-7}$ linear, branched or cyclic alkyl or alkenyl group or a phenyl group optionally substituted,
  a $C_1$-$C_{10}$ sulfonyl group, or
  a $C_1$-$C_{10}$ hydrocarbon group optionally comprising up to four heteroatoms selected from the group consisting of oxygen, nitrogen, silicium or sulfur, provided that said heteroatom is not directly bonded to the oxygen atom bearing said R group.

According to a particular embodiment of the invention, R represents a hydrogen atom, a $C_{1-6}$ linear, branched or cyclic alkyl, alkenyl or acyl group optionally substituted, an optionally substituted benzyl group, a $C_1$-$C_{10}$ sulfonyl group, such as a $MeSO_2$, $CF_3SO_2$, $C_6H_5SO_2$ or $CH_3C_6H_4SO_2$, a group of formula —$CH(R^a)OCH_2R^a$, $R^a$ representing a hydrogen atom or a $C_{1-5}$ alkyl group or, taken together, representing a $C_1$-$C_5$ group, or a group of formula $Si(R^3)_3$, $R^3$ representing a $C_{1-7}$ linear, branched or cyclic alkyl or alkenyl group or a phenyl group optionally substituted.

According to a particular embodiment of the invention, R represents a hydrogen atom, a $C_{1-6}$ linear vinyl or acyl group, a group of formula —$CH(R^a)OCH_2R^a$, $R^a$ representing a hydrogen atom or a $C_{1-5}$ alkyl group or, taken together, representing a $C_1$-$C_5$ group, or a group of formula $Si(R^3)_3$, $R^3$ representing a $C_{1-3}$ linear alkyl.

As mentioned above, R, $R^1$, $R^2$ and $R^3$ can be substituted, for example, by up to two groups. As non-limiting examples, said groups are $C_{1-5}$ alkyl, alkoxy or cycloalkyl group.

The compound of formula (I), in any of its embodiments, possesses three asymmetric carbon atoms on the cyclohexenone ring, namely carbon atoms 2, 3 and 5. Therefore, said compound can be in the form of any one of its stereoisomers. Furthermore it is also understood that the invention's compound can be in the form of a mixture of any one of said stereoisomers.

According to an embodiment of the invention, the invention's compounds are trans ketones of formula (II)

wherein R, $R^1$ and $R^2$ have the same meaning as indicated in formula (I) and the groups OR and $R^2$ are in a relative configuration trans.

According to a further embodiment, the compounds of formula (II) are in an optically active form of formula

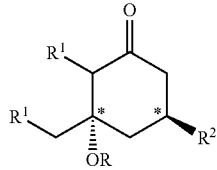

(III)

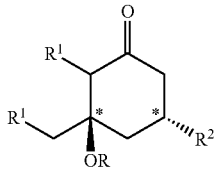

(III')

wherein R, $R^1$ and $R^2$ have the same meaning as indicated in formula (I) and the asterisks mean the configuration of the carbon is absolute and therefore that said compound (III) or (III') is in an optically active form.

In particular, said compound (III) is in the form of a mixture of the compounds of formula

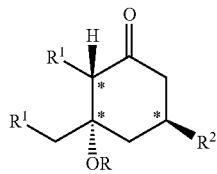

(IV)

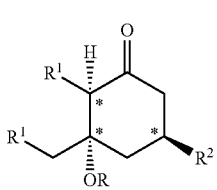

(IV')

wherein R, $R^1$ and $R^2$ have the same meaning as indicated in formula (I) and the asterisks mean the configuration of the carbon is absolute and therefore that said compound (IV) or (IV') is in an optically active form.

According to another embodiment of the invention, and independently of the fact that the compound is of formula (I), (II), (III), (III') (IV) or (IV'), the $R^1$ groups, taken separately, are identical and represent an achiral $C_{1-5}$ linear, branched or cyclic alkyl or alkenyl group or alternatively said two $R^1$, taken together, represent a linear $C_3$-$C_{10}$ alkanediyl or alkenediyl group;

$R^2$ represents an achiral $C_{1-5}$ linear or branched alkyl or alkenyl group or a phenyl group; and R represents a hydrogen atom, a $C_{1-5}$ linear, branched or cyclic alkyl or alkenyl group optionally substituted, a benzyl group, a group of formula —CH($R^a$)OCH$_2R^a$, $R^a$ representing a hydrogen atom or a methyl, ethyl or n-propyl group or, taken together, representing a $C_3$-$C_4$ group, or a group of formula Si $(R^3)_3$, $R^3$ representing a $C_{1-5}$ linear, branched alkyl group or a phenyl group.

Alternatively the $R^1$ groups, taken separately, are identical and represent an achiral $C_{1-5}$ linear, branched or cyclic alkyl group or alternatively said two $R^1$, taken together, represent a linear $C_3$-$C_{10}$ alkanediyl or alkenediyl group;

$R^2$ represents an achiral $C_{1-5}$ linear or branched alkyl group or a phenyl group; and R represents a hydrogen atom, a $C_{1-5}$ linear, branched or cyclic alkyl group optionally substituted, a group of formula —CH($R^a$)OCH$_2R^a$, $R^a$ representing a hydrogen atom or a methyl, ethyl, isopropyl or propyl group or, taken together, representing a $C_3$-$C_4$ group, or a group of formula Si $(R^3)_3$, $R^3$ representing a $C_{1-4}$ linear or branched alkyl group or a phenyl group.

Yet, independently from the specific embodiment, R may represent only a hydrogen atom or may represent a Si($R^3)_3$ group, $R^3$ representing a $C_{1-4}$ alkyl group or a phenyl group, or a group of formula —CH($R^a$)OCH$_2R^a$, $R^a$ representing a hydrogen atom or a methyl, ethyl or isopropyl group or, taken together, representing a CH$_2$CH$_2$ or CH$_2$CH$_2$CH$_2$ group.

In said embodiments, the optional substituents are defined as above.

Specific examples of said compounds are:
(–)-(1R,11S,14R)-1-Hydroxy-14-methyl-bicyclo[9.4.0]pentadecan-12-one, (–)-(1R,11R,14R)-1-Hydroxy-14-methyl-bicyclo[9.4.0]pentadecan-12-one, (1RS,11RS,14RS)-1-Hydroxy-14-methyl-bicyclo[9.4.0]pentadecan-12-one, (1RS,11RS,14RS)-1-ethoxyethoxy-14-methylbicyclo[9.4.0]pentadecan-12-one, and (1RS,11RS,14RS)-14-methyl-1-trimethylsilyloxybicyclo[9.4.0]pentadecan-12-one.

A second object of the present invention is a process for the preparation of an optically active compound of formula

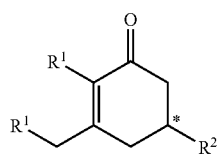

(V)

wherein the $R^1$, $R^2$ and the asterisk have the same meaning as indicated above, for the various embodiment of compound (I), by treating a trans ketone of one of formulae

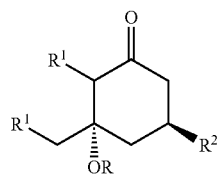

(II)

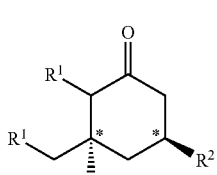

(III)

-continued

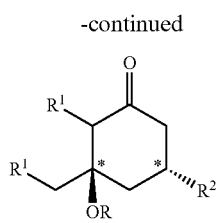
(III')

wherein the asterisk, $R^1$ and $R^2$ have the meaning indicated above and R is as defined above provided that it is not a hydrogen atom;
with an optically active sodium or potassium alkoxide and optionally a means of removing water; or
by treating an optically active trans ketone of formula (III) or (III')

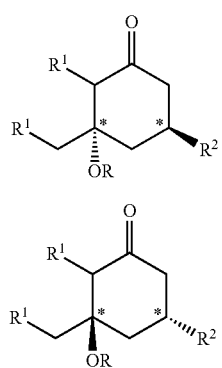
(III)

(III')

wherein $R^1$ and $R^2$ have the meaning indicated above and R is hydrogen
with a $C_1$-$C_8$ sulfonyl chloride in the presence of a tertiary $C_3$-$C_{24}$ amine.

By "optically active alkoxide" we mean here a compound comprising at least one moiety having an alkoxy group, i.e. a deprotonated alcohol group, and which is optically active. In other words, said optically active alkoxide can be an optically active sodium or potassium salt of a $C_4$-$C_{40}$ compound comprising one, two or three of such moieties or of a carbohydrate or a derivative thereof, such as a sugar, or of a polymer comprising optically active alkoxy groups.

Although it is not possible to provide an exhaustive list of the currently known optically active sodium or potassium alkoxides which can be used in the invention's process, the following can be named as preferred examples:

a) a sodium or potassium salt of a $C_4$-$C_{18}$ optically active mono alcohol, such as a sodium or potassium salt of an optically active alcohol of formula

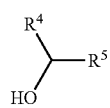
(A)

wherein $R^5$ represents a $C_{1-4}$ alkyl group or an optionally substituted phenyl group and $R^4$ represents a $C_{1-4}$ alkyl group or a $C(R^{5'})_2(OR^{4'})$ group, $R^{5'}$ representing a hydrogen atom or a $R^5$ group and $R^{4'}$ representing a $C_{1-6}$ alkyl group or a $C_{3-9}$ trialkyl silyl or a triphenyl silyl group; or such as a chiral alcohol of formula $R^{4''}$—OH, wherein $R^{4''}$ represents a $C_{7-12}$ chiral hydrocarbon group;

b) a sodium or potassium salt of
a $C_3$-$C_{18}$ optically active 1,2-diol, such as a sodium or potassium salt of an optically active diol of formula

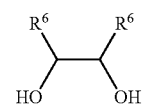
(B)

wherein $R^6$ represents an optionally substituted phenyl group, a $C_{1-6}$ alkyl group or a $COOR^7$ group, $R^7$ representing a $C_{1-4}$ alkyl group;

a $C_4$-$C_{18}$ optically active 1,3-diol, such as a sodium or potassium salt of an optically active diol of formula

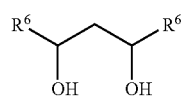
(C)

wherein R has the meaning indicated above;
a $C_5$-$C_{35}$ optically active 1,4-diol, such as a sodium or potassium salt of an optically active diol containing a moiety of formula

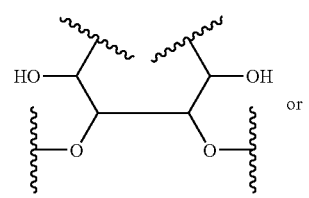
(D)

or

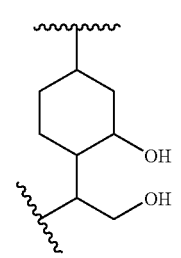
(D')

or such as a sodium or potassium salt of an optically active diol of formula

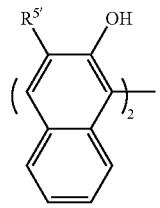
(D″)

wherein $R^{5'}$ has the meaning indicated above;

c) a sodium or potassium salt of a $C_4$-$C_{25}$ optically active alcohol containing a nitrogen in the βposition, such as a sodium or potassium salt of an optically active 1,2-aminoalcohol of formula

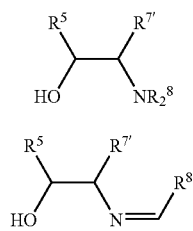
(E)
(E')

wherein $R^5$ has the meaning indicated above, R represents a $R^4$ or R group as defined above and $R^8$ represents an optionally substituted phenyl group, a $C_{1-9}$ alkyl or alkylbenzene group a $SiR^{7'}_3$ group or a $R^{7'}CO$ group; optionally $R^5$ and $R^{7'}$ can be bonded together to form a $C_{5-10}$ ring or $R^{7'}$ and a $R^8$ can be bonded together to form a $C_{4-5}$ heterocycle, or the two $R^8$ can be bonded together to form a $C_{2-5}$ heterocycle;

or such as a sodium or potassium salt of an optically active iminoalcohol of formula

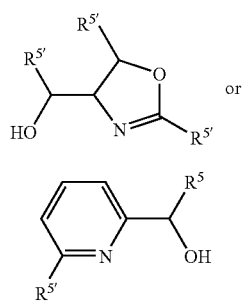
(F)
(F')

wherein $R^5$ and $R^{5'}$ have the meaning indicated above;

d) a sodium or potassium salt of a $C_{15-38}$ compound having two or three groups derived from an optically active alkoxide mentioned under a), b) or c); or e) a sodium or potassium salt of an optically active alkoxide mentioned under d) and which is supported on an insoluble material such as silica, Merrifield resins, gold or polystyrenes.

Examples of substituents of phenyl groups are $R^b$, $SR^b$, $NO_2$ or $OR^b$ groups or yet halogen atoms, wherein $R^b$ stands for a $C_{1-4}$ alkyl group.

According to a particular embodiment of the invention, said optically active sodium or potassium alkoxide comprises one or two alkoxy groups and is:

a) a sodium or potassium salt of an optically active alcohol of formula

(G)

wherein $R^9$ represents a $C_{1-4}$ alkyl group and $R^{10}$ represents a phenyl group optionally substituted by one $C_{1-4}$ alkyl group;

b) a sodium or potassium salt of an optically active 1,2-diol of formula

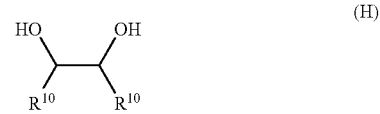
(H)

wherein $R^{10}$ has the meaning indicated above;
or a sodium or potassium salt of an optically active 1,4-diol of formula

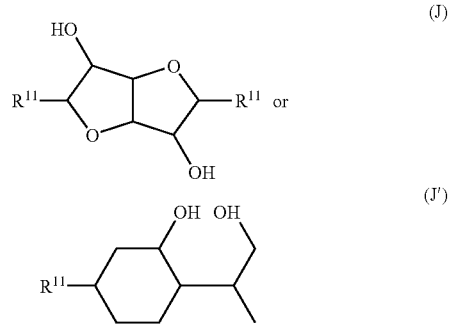
(J)
(J')

wherein $R^{11}$ represents a $C_{1-4}$ group or a hydrogen atom;

c) a sodium or potassium salt of an optically active 1,2-amino alcohol of formula

(K)

wherein $R^{12}$ represents a phenyl group optionally substituted by a SMe, OMe, $NO_2$ or $C_{1-4}$ alkyl group, $R^{13}$ represents a $C_{1-4}$ alkyl group, a $R^{12}$ group or a $CH_2OSiMe_2{}^tBu$ group and $R^{14}$ represents a benzyl or $C_{1-4}$ alkyl, or the two $R^{14}$ are bonded together to form a $C_{4-5}$ heterocycle;

or a sodium or potassium salt of an optically active 1,2-imino alcohol of formula (L)

wherein R$^{12}$ has the meaning indicated above; or
d) a sodium or potassium salt of an optically active alcohol of formula (M)

wherein R$^{12}$ has the meaning indicated above.

The invention's processes using the 1,2-amino alcohols of formula (E), (E') or (K) represents a particularly appreciated embodiment of the invention.

Specific examples of the above-mentioned optically active sodium or potassium alkoxides are a sodium or potassium salt of a compound of formula I to 12 (the absolute configuration being represented in the drawings):

a)

(1)

b)

(2)

c)

(3)

(4)

(5)

(6)

(7)

(8)

(8')

(9)

-continued

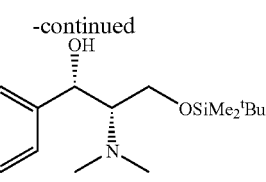
(10)

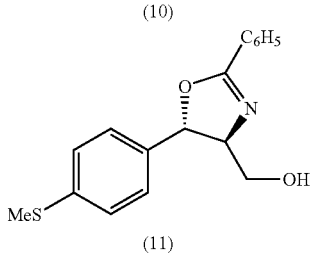
(11)

d)

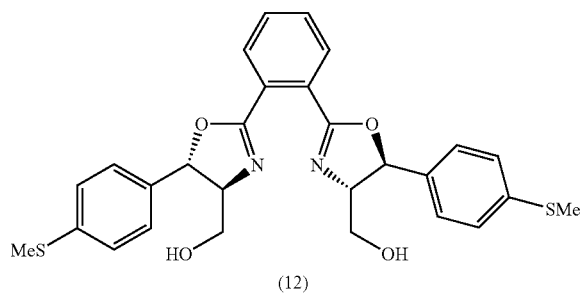
(12)

said compounds having proved to be particularly useful for the invention's process wherein the starting compound (I) is a bicycle.

It is also useful to mention that the optically active alkoxide can be characterized by a specific enantiomeric excess (e.e.). In general, optically active alkoxide having a higher e.e. provided compounds (V) with higher e.e. Therefore, it is preferable to employ in the invention's process optically active alkoxide having e.e. of at least 50% or even of at least 90%.

The optically active alkoxide can be added to the reaction medium in a large range of concentration. As non-limiting examples, one can cite as optically active alkoxide concentration values ranging from 0.05 to 8.0 molar equivalents, relative to the ketone (I). Preferably, the optically active alkoxide concentration will be comprised between 0.1 and 4.0 molar equivalents. It goes without saying that the optimum concentration of said alkoxide will depend on the nature of the latter and on the desired time of reaction.

The chiral sodium or potassium alkoxide can be in the form of a preformed salt or it can be formed in situ prior to its use, e.g. by pre-mixing a chiral compound comprising at least one moiety having a hydroxy group and an appropriate sodium or potassium base.

According to a particular embodiment of the invention, particularly appreciated alkoxides are the 1,2-amino alcohols, and in particular the ones cited above.

As mentioned above, the process can be performed in the presence of a means of removing water. According to a preferred embodiment of the invention, the process is carried out in the presence of said water-removing means.

By "a means of removing water" we mean here a compound or a substance capable of trapping the water which is formed during the reaction. Said water can be trapped either by means of an absorption mechanism or by means of a chemical reaction or also by azeotropic distillation.

Examples of useful water-removing means are:
i) an alkaline or alkaline earth hydride, such as NaH, KH, $CaH_2$, LiH;
ii) a reaction-medium insoluble inorganic material capable to form a clathrate with water, such as an anhydrous zeolite, preferably of the 4 Å type, or anhydrous $MgSO_4$, $Na_2SO_4$, $Na_2O$, $CaCl_2$ or $MgCl_2$; or
iii) an organic material capable of reacting with water to form non-acidic compounds, such as an orthoester, N-methyl-N-trimethylsilyl-trifluoroacetamide or 1-trimethyl-silylimidazole.

The water-removing means can be added to the reaction medium in a large range of amounts which depend on the exact nature of the water-removing means. In general, it has been observed that the higher the amount of means of removing water employed, the higher is the e.e. of the compound (V) obtained at the end of the process. However, the addition of amounts which exceed three times the amount theoretically needed to trap all the water which can theoretically be formed does not provide any appreciable additional benefit.

Concerning the sulfonyl chloride one may cite, as non-limiting examples, $MeSO_2Cl$, $CF_3SO_2Cl$, $MeC_6H_4SO_2Cl$ or $C_6H_5SO_2Cl$. Concerning the amine one may cite, as non-limiting examples, triethyl or tributyl amine or yet DBU. Said amine can be in a racemic or optically active form and is conveniently added in at least an equimolar amount with respect to the staring ketone (III) or (III').

This process of the invention, in any of its embodiments, can be carried out in the presence or in the absence of solvent, but in any case it is advantageously performed under anhydrous conditions. As a person skilled in the art can anticipate, the presence of a solvent is mandatory only in the case in which the starting ketone is a solid compound under the reaction conditions.

However, according to a preferred embodiment of the invention, and independently of the physical state of the starting ketone, the process is advantageously carried out in the presence of a solvent. Said solvent must be chemically compatible with the reaction and does not deactivate the alkoxide.

A suitable solvent is one which is aprotic. Non-limiting examples of such a solvent are ethers, esters, amides, aromatic hydrocarbons, linear or branched or cyclic hydrocarbons, chlorinated solvents and mixtures thereof. More preferably, the solvent is a $C_4$-$C_6$ ether such as THF or dioxane, $C_3$-$C_6$ amides such as DMF or N-Methyl pyrrolidone, methylene chloride, toluene, N-methyl morpholine and mixtures thereof.

The temperature at which this process of the invention can be carried out, in any of its embodiments, is comprised between −80° C. and 100° C., preferably between −78° C. and 20° C. Of course a person skilled in the art is also able to select the preferred temperature as a function of the melting and boiling point of the starting and final products and/or an eventual solvent.

A third object of the present invention concerns a process for the preparation of the invention's compounds (I), i.e. a process for the preparation of a compound of formula (I), as defined above, comprising the step of:

a) treating an achiral di-ketone of formula

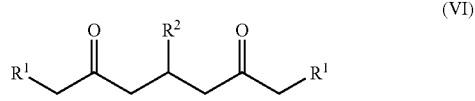
(VI)

wherein R¹ and R² have the same meaning as indicated above, for the various embodiment of compound (I), with a $C_3$-$C_{24}$ amine or diamine, in a racemic or optically active form; and in the presence of a complex obtainable by admixing $TiCl_4$ or $ZrCl_4$ with an equimolar amount of an alcohol $R^bOH$, $R^b$ representing a $C_1$-$C_5$ alkoxy group, or of a chiral ligand selected from the group consisting of an optically active alcohol of formula (E), (E'), (F) or (F'), as defined above, and an optically active alcohol of formula

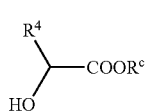
(N)

wherein $R^4$ has the meaning indicated above and $R^c$ represents a $C_{1-4}$ alkyl group;

b) hydrolyze the reaction medium of step a) to obtain a compound of formula (I) wherein R is a hydrogen atom; and c) converting the compound obtained in step b), by treating it with an appropriate reagent, into a compound of formula (I) wherein R is not a hydrogen atom.

The exact nature of said "appropriate reagent" is well known by the person skilled in the art, and several examples are given in basic text books of chemistry (e.g. T. H. Greene and P. G. M. Wuts, "Protective Groups in Organic Synthesis", John Wiley & Sons, Inc., 3$^{rd}$ edition, 1999; in particular from page 17 to page 200). Although it is not possible to provide a detailed list, which in any case would not be exhaustive, of said appropriate reagents. However, as non-limiting examples one may cite the following reagents:

a compound of formula RX, R having the meaning of formula (I), and X being a $C_{1-6}$ sulfonate or a halogen atom;

an appropriate carboxylic anhydride or chloride, i.e. susceptible to provide a R group which is an acyl;

a compound of formula $XCH(R^a)OCH_2R^a$, or of formula $HR^{a'}C=CHOCH_2R^a$, $R^{a'}$ representing a $R^a$ group without a $CH_2$ group and $R^a$ having the meaning indicated above;

an appropriate alkene, i.e. susceptible to provide a R group which is an alkyl or alkenyl group.

It is well understood by a person skilled in the art that the use of a complex comprising an optically active ligand, such as one of formula (E), will lead to the formation of a compound (I) in an optically active form, i.e. a compound of formula (III) or (III'), while the use of a complex comprising a ligand that is not optically active, such as OPr, will lead to the formation of a compound (I) in a racemic form, and in particular to a compound of formula (II).

According to a particular embodiment of the invention, the preferred complex is obtained by admixing $TiCl_4$ with n-propyl or iso-propyl alcohol.

According to a particular embodiment of the invention, the preferred chiral ligands are of formula (K) or (L), as defined above, and in particular of formula (6), (7), (8), (8') or (9), as defined above.

According to another particular embodiment of the invention, the preferred RX is a compound of formula Si $(R^3)_3X$, $R^3$ representing a $C_1$-$C_4$ alkyl group or a phenyl group and X representing a chloride atom or a $CF_3SO_3$ group.

According to another particular embodiment of the invention, the preferred compound of formula $XCH(R^a)OCH_2R^a$, or of formula $HR^{a'}C=CHOCH_2R^a$, are those wherein $R^a$ or $R^a$, taken separately, represents a hydrogen atom or a methyl, ethyl, propyl or isopropyl group, or $R^a$ and $R^a$, taken together, represents a $CH_2CH_2$ or $CH_2CH_2CH_2$ group.

Said process can be advantageously carried out in a solvent selected from the group of N-methyl-morpholine, $CH_2Cl_2$, DMF or NMP. Furthermore, the process can be carried out at a temperature comprised between −10° C. and 30° C. Said solvent may further comprise water.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 360 MHz or 100 MHz machine for $^1H$ or $^{13}C$ respectively, the chemical displacements δ are indicated in ppm with respect to TMS as standard, the coupling constants J are expressed in Hz.

The cyclic 3-methyl-1,5-diones were prepared according to the reference G. Ohloff, J. Becker, K. H. Schulte-Elte, *Helv. Chim. Acta* 1967, 50, 705.

Example 1

Preparation of (−)-(1R,11S,14R)-1-hydroxy-14-methyl-bicyclo[9.4.0]-pentadecan-12-one (13) and (−)-(1R,11R,14R)-1-hydroxy-14-methyl-bicyclo[9.4.0]-pentadecan-12-one (14)

Preparation of catalyst: A solution of freshly distilled (+)—N-isopropylephedrine (10.35 g, 50.0 mmol) in $CH_2Cl_2$ (150 ml) was treated in 5 minutes with a solution of $TiCl_4$ (9.50 g (5.52 ml); 50 mmol) in $CH_2Cl_2$ (50 ml) (temp. 30 to 40° C.). After introduction, the solvent was distilled under $N_2$. The residue was dried under vacuum (0.01 mbar): 21.77 g.

Aldol reaction: The above obtained catalyst (20.71 g; max. 47.6 mmol; 0.80 equiv) was poured under stirring into a 250 ml vessel containing NMP (57 ml). The temperature was allowed to reach 34° C. After 5 minutes, solid 3-methyl-1,5-cyclopentadecanedione (15) (14.98 g, 59.4 mmol) was added to the stirred dark brown solution. After 5 minutes, the solution was treated under ice-cooling with TMEDA (6.67 g, 8.54 ml, 57.5 mmol) containing $H_2O$ (89.1 mg; 4.95 mmol). The temperature was maintained at 0-2° C. After 165 min, the turbid reaction mixture was poured into 5% HCl/ice and extracted with ether. The organic phases were washed ($H_2O$ (2×), saturated $NaHCO_3$, NaCl), dried ($Na_2SO_4$) and evaporated. Flash chromatography, using $SiO_2$ (350 g) and cyclohexane/AcOEt=9:1 afforded successively (15) (4.95 g, 33%) and (13)/(14) (ca. 1:1) (9.97 g, 66.5%). Two parallel flash chromatographies, using $SiO_2$ (300 g) and cyclohexane/AcOEt=9:1, afforded together successively 4.35 g (yield: 29%) of (14) (17% ee), 0.95 g (yield: 6%) of (13)/(14) and 3.85 g (yield: 26%) of (13) (42% ee).

The enantiomeric excesses were determined by using a chiral capillary column CP-Chirasil-DEX CB (25 m×0.25 mm) (Chrompack) and as carrier gas He at 0.63 bar of the corresponding silylated diol of alcool.

Spectra of (13):
$^1$H-NMR: 1.01 (d, J=6.5, 3H); 1.20-1.68 (m, 20H); 1.74 (m, 1H); 2.18-2.45 (m, 4H).
$^{13}$C-NMR: 214.2 (s); 78.3 (s); 58.67 (d); 44.8 (t); 42.5 (t); 37.8 (t); 27.7 (d); 26.8 (t); 26.4 (t); 25.7 (t); 25.5 (t); 25.1 (t); 25.0 (t); 24.9 (t); 22.0 (q); 18.6 (t).

Spectra of (14):

$^1$H-NMR: 1.02 (d, J=6.5, 3H); 1.08 (m, 1H); 1.20-1.73 (m, 18H); 1.85 (m, 1H); 1.96 (t, J=13, 1H); 2.14 (m, 1H); 2.36 (m, 1H); 2.41 (m, 2H).

$^{13}$C-NMR: 211.0 (s); 79.7 (s); 55.7 (d); 49.9 (t); 45.0 (t); 39.7 (t); 28.7 (d); 26.9 (t); 26.4 (t); 26.2 (t); 26.0 (t); 25.2 (t); 25.0 (t); 22.2 (t); 22.1 (q); 19.3 (t).

Alternatively, in the above experiment, the crude product obtained after drying over $Na_2SO_4$ was dissolved in hot heptane (420 ml) and let stand at 23° C. for 15 hours. After filtration of the crystals, the mother liquors were purified by chromatography, using $SiO_2$ (270 g) and cyclohexane/AcOEt=9:1, then 7:3. The apolar fractions afforded (15) (5.82 g; 39%), the polar ones a mixture of (13)/(14) (44:56 by GC of derived diols); (yield: 28%)). Flash chromatography, using $SiO_2$ (250 g) and cyclohexane/AcOEt=9:1, afforded successively 1.96 g (yield: 13%) of (14) (44% ee), 0.41 g (yield: 3%) of (13)/(14) and 1.54 g (yield: 10%) of (13) (75% ee).

$[\alpha]_D^{20}$ ($CHCl_3$; c=0.98)-25.7 (extrapolation for enantiomerically pure (13): $[\alpha]_D^{20}$-34). $[\alpha]_D^{20}$ ($CHCl_3$; c=2.9)-17.1 (extrapolation for enantiomerically pure (14): $[\alpha]_D^{20}$-39).

Example 2

Preparation of (1RS,11RS,14RS)-1-hydroxy-14-methyl-bicyclo[9.4.0]-pentadecan-12-one (16)

A solution of (15) (15.12 g, 60.0 mmol) in $CH_2Cl_2$ (210 ml) was treated at 22-24° C. with a solution of $ZrCl_3OPr$ (36% in AcOEt) (65.25 g, 91.6 mmol). After 5 minutes, the yellowish solution was treated at –10-0° C. with $NBu_3$ (19.43 g, 25.0 ml, 105 mmol). After 15 minutes, the reaction mixture was poured into water and extracted with ether. The organic phases were washed ($H_2O$, saturated $NaHCO_3$, NaCl), dried ($Na_2SO_4$) and evaporated. Crystallization from heptane (345 ml) afforded 11.93 g of (16) (yield: 79%) and 2.80 g of mother liquors, from which another 1.39 g (yield: 9%) of (16) were recovered. Same spectra as (14).

Example 3

Preparation of (+)-(S)-14-methylbicyclo[9.4.0]-pentadec-1(11)-en-12-one (17)

A solution of (13)/(14) (9.97 g; 39.56 mmol) (obtained from the repetition of Example 1 after one chromatography) in $CH_2Cl_2$ (300 ml) was treated with $Me_3N$—HCl (1.89 g; 19.80 mmol). At –15° C., the stirred mixture was treated successively with $NEt_3$ (15.98 g, 158.2 mmol) and drop-wise with MsCl (13.58 g, 118.7 mmol). The reaction mixture was stirred at 0° C. for 1 h and at 25° C. for 15 hour. It was then poured into 5% HCl and extracted with ether. The organic phases were washed ($H_2O$, saturated $NaHCO_3$, NaCl), dried ($Na_2SO_4$) and evaporated to give a crude oil. The oil was heated in toluene (60 ml) and DBU (9.02 g, 59.34 mmol) for 1 hour at 80° C., cooled and worked up as above (5% HCl and extraction). Bulb-to-bulb distillation (oven temp. 100-150° C./0.01 mb) afforded 8.72 g (yield: 94%) of (17) (29% ee).

Example 4

Preparation of (1RS,11RS,14RS)-1-ethoxyethoxy-14-methylbicyclo[9.4.0]-pentadecan-12-one (18)

A mixture of 2 g (7.9 mmol) of (16) and 0.84 ml (8.7 mmol) ethyl vinyl ether in 2 ml THF was stirred at room temperature in the presence of 20 µl (0.32 mmol) trifluoroacetic acid for 2 days. After a short column filtration ($SiO_2$) using diethyl ether as eluent and evaporation of the solvent 2.6 g of the crude product (18) was obtained. Flash chromatography, using $SiO_2$ and cyclohexanelEtOAc=95:5 as eluent, afforded 2.10 g (82%) of (18) as a ~1:1 mixture of diastereomers.

First Isomer:
$^1$H-NMR: 0.98 (d, J=6.2, 3H), 1.12 (t, J=6.7, 3H), 1.17 (d, J=5.1, 3H), 1.26-1.82 (m, 19H), 1.84-1.96 (m, 2H), 2.08-2.16 (m, 1H), 2.34 (d, J=8.2, 1H), 2.38-2.42 (m, 1H), 3.37-3.43 (m, 2H), 4.97 (q, J=5.1, 1H).

$^{13}$C-NMR: 15.5, 19.8, 20.7, 22.1, 22.4, 25.1, 25.2, 25.8, 26.0, 26.6, 27.2, 28.2, 33.7, 43.2, 49.8, 56.6, 57.9, 84.8, 93.4, 210.6.

Second Isomer:
$^1$H-NMR: 0.99 (d, J=6.2, 3H), 1.16 (t, J=6.7, 3H), 1.17 (d, J=5.6, 3H), 1.22-1.99 (m, 21H), 2.16-2.24 (m, 1H), 2.35 (d, J=8.2, 1H), 2.39-2.43 (m, 1H), 3.40-3.59 (m, 2H), 4.90 (q, J=5.6, 1H).

$^{13}$C-NMR: 15.5, 19.6, 20.8, 22.1, 22.5, 25.2, 25.2, 25.9, 26.2, 26.4, 27.2, 28.4, 35.0, 40.5, 49.7, 56.4, 56.4, 85.2, 92.1, 210.3.

Example 5

Preparation of (1RS,11RS,14RS)-14-methyl-1-trimethylsilyloxybicyclo[9.4.0]pentadecan-12-one (19)

A mixture of 25 mg (0.1 mmol) of (16) and 17 µl (0.12 mmol) triethyl amine in 0.5 ml THF was treated at 0° C. with 21 µl (0.11 mmol) TMSOTf. After 30 min 8 µl (0.06 mmol) triethyl amine and 10 µl (0.055 mmol) TMSOTf were added. After 10 min the mixture was diluted with diethyl ether and was poured into 2 ml of a saturated $NH_4Cl$ solution. The organic phase was separated, diluted with 3 ml of dichloro methane and the solvent was evaporated at room temperature under vacuum to afford 32 mg (19) (yield: 99%).

$^1$H-NMR: 0.1 (s, 9H), 0.99 (d, J=6.6, 3H), 1.18-1.67 (m, 18H), 1.87-1.93 (m, 2H), 2.04-2.22 (m, 2H), 2.28 (d, J=8.2, 1H), 2.35-2.40 (m, 1H).

$^{13}$C-NMR: 2.6 (3C), 19.9, 22.1, 22.6, 25.1, 25.2, 26.1, 26.3, 26.3, 27.2, 28.7, 39.1, 45.6, 49.9, 56.8, 83.4, 210.9.

Example 6

Preparation of (+–)-3-butyl-r-3-hydroxy-t-5-methyl-c-2-propylcyclohexanone (20) and (+–)-3-butyl-r-3-hydroxy-t-5-methyl-t-2-propylcyclohexanone (21)

a) Preparation of 7-methyl-5,9-tridecanedione 75 ml (1.03 mol) $SOCl_2$ were added in 20 min to 50 g (0.34 mol) 3-methylglutamic acid (in a 250 ml flask with reflux condenser connected to two washing bottles: 250 ml $H_2O$, 250 ml 20% NaOH) at roomtemperature under stirring. After adding 0.5 ml pyridine an evolution of gas was observed and the temperature decreased (5-10° C.). The mixture was heated to an internal temperature of 25° C. for 30 min and stirred for 22 hours at room temperature. Distillation through a Vigreux column at 60° C./2.1 mbar afforded 48.57 g (78%, 0.27 mol) of the diacid chloride as a colourless liquid.

125 ml (0.25 mol) of a solution of n-buthylmagnesium chloride (2.0 M in THF) were added within 45 minutes at a temperature between –2 and 0° C. to a mechanically stirred solution of the diacid chloride (22.9 g, 0.125 mol), $MnCl_4Li_2$ in THF (20 ml, ca. 12.5 mmol), CuCl (0.71 g, 7.1 mmol) and THF (200 mL). After 75 min at 0° C. the mixture was poured onto 150 ml of a cooled 2NHCl solution. The aqueous phase was extracted with diethyl ether (3×100 ml) and the combined organic phases were washed with water (3×50 ml, pH 7) and dried over $Na_2SO_4$. After filtration and evaporation of the solvent the crude product (29.6 g) was distilled through a Vigreux column (15 cm) at 115° C./0.35 mbar affording 19.4 g of 7-methyl-5,9-tridecanedione (69%, 0.086 mol).

$^1$H-NMR: 0.90 (t, J=7.7, 6H), 0.92 (t, J=6.7, 3H), 1.28 (sextet, J=7.7, 4H), 1.54 (q, J=7.7, 4H), 2.29 (dd, J=15.9, J=7.2, 2H), 2.38 (t, J=7.7, 4H), 2.42 (dd, J=15.9 Hz, J=5.6, 2H), 2.51 (sextet, J=6.7, 1H).

$^{13}$C-NMR: 13.9 (2C), 20.3, 22.4 (2C), 25.5, 25.9 (2C), 42.9 (2C), 49.2 (2C), 210.6 (2C).

b) Preparation of the Desired Products

A solution of 7-methyl-5,9-tridecanedione (250 mg, 1.1 mmol) in 4-methylmorpholine (1.1 mL) was treated at 25° C. with a 0.675 g (1.1 mmol) of solution of $TiCl_3OiPr$ (1.637 mmol Ti/g in AcOEt). After 15 min the mixture was diluted with diethyl ether and treated with a cold solution of 2N HCl. After extraction with diethyl ether the organic phases were washed (sat. $NaHCO_3$, $H_2O$), dried ($Na_2SO_4$) and evaporated (crude 250 mg). Flash chromatography, using $SiO_2$ (23 g) and n-pentane/AcOEt=85:15, afforded successively 178 mg (yield: 72%) of (20) and 8 mg (yield: 4%) of (21).

Spectra of (20):
$^1$H-NMR: 0.91 (t, J=7.2, 3H), 0.94 (t, J=7.6, 3H), 1.02 (d, J=6.1, 3H), 1.08-1.68 (m, 11H), 1.76-1.86 (m, 2H), 2.00 (t, J=12.3, 1H), 2.17-2.30 (m, 2H), 2.37-2.41 (m, 1H).

$^{13}$C-NMR: 14.0, 14.4, 22.1, 22.2, 23.2, 23.9, 26.6, 29.5, 41.2, 44.8, 50.4, 56.6, 79.0, 211.0.

Spectra of (21):
$^1$H-NMR: 0.91 (t, J=7.2, 3H), 0.93 (t, J=6.7, 3H), 1.02 (d, J=6.7, 3H), 1.16-1.70 (m, 13H), 2.10 (t, J=13.3, 1H), 2.20-2.28 (m, 3H).

$^{13}$C-NMR: 14.0, 14.1, 20.4, 22.1, 23.1, 24.0, 28.6, 31.2, 39.7, 40.9, 45.6, 60.2, 77.5, 214.1.

Example 7

Preparation of (+−)-3-butyl-r-3-(1-ethoxyethoxy)-t-5-methyl-c-2-propylcyclohexanone (22)

A mixture of 666 mg (2.95 mmol) of (21) and 1.13 mL (11.8 mmol) ethyl vinyl ether was stirred at room temperature in the presence of 13 mg Amberlyst® 15 for 18 hour. Flash chromatography of the brown mixture, using $SiO_2$ (88 g) and n-pentane/$Et_2O$=9:1, afforded 626 mg (yield: 71%) of (22) as a ~1:1 mixture of diastereomers.

$^1$H-NMR: 0.87-0.97 (m, 12H), 0.99 (d, J=6.1, 3H), 1.00 (d, J=5.1, 3H), 1.10-1.98 (m, 40H), 2.21-2.25 (m, 2H), 2.35-2.38 (m, 2H), 3.36-3.57 (m, 4H), 4.89 (q, J=5.1, 1H), 4.96 (q, J=5.2, 1H).

$^{13}$C-NMR: 14.0, 14.1, 14.1, 14.5, 14.5, 15.4, 15.5, 20.6, 20.8, 22.1, 22.1, 22.2, 23.4, 23.4, 24.3, 24.6, 27.4, 27.5, 28.8, 29.0, 35.6, 37.1, 40.7, 43.4, 50.1, 50.2, 56.1, 56.4, 56.5, 57.9, 84.0, 84.3, 92.2, 93.5, 210.1, 210.6.

Example 8

Preparation of (+−)-3-butyl-r-3-(trimethylsilyloxy)-t-5-methyl-c-2-propylcyclohexanone (23)

A mixture of 56 mg (0.25 mmol) of (21) and 49 µl (0.35 mmol) triethylamine in 1 ml THF was treated at 0° C. with 58 µl (0.30 mmol) TMSOTf. After 30 min the mixture was diluted with 5 ml diethyl ether and was poured onto 2 ml of a sat. $NH_4Cl$ solution with 2 g ice. After extraction with diethyl ether (2×) the organic phases were washed (saturated $NH_4Cl$), dried ($Na_2SO_4$) and evaporated to afford 65 mg (23) (0.22 mmol, yield: 88%).

$^1$H-NMR: 0.0 (s, 9H), 0.86 (t, J=7.2, 3H), 0.90 (t, J=7.7, 3H), 0.94 (d, J=6.7, 3H), 1.03-1.49 (m, 8H), 1.61-1.65 (m, 2H), 1.72-1.83 (m, 2H), 1.88 (t, J=12.8, 1H), 2.12-2.17 (m, 2H), 2.28-2.30 (m, 1H).

$^{13}$C-NMR: 2.6 (3C), 14.1, 14.6, 21.9, 22.0, 23.3, 24.6, 27.5, 29.3, 40.9, 45.8, 50.3, 56.5, 82.7, 210.7.

Example 9

Preparation of (1RS,11RS,14RS)-1-vinyloxy-14-methylbicyclo[9.4.0]-pentadecan-12-one (26)

A mixture of 1 g (4 mmol) of (16) and 0.46 ml (4.8 mmol) ethyl vinyl ether in 2 ml THF was stirred at room temperature in the presence of 201 mg (0.8 mmol) pyridinium p-toluenesulfonate (PPTS) for 4 hours. The mixture was stirred at 40° C. for 2 h and 0.46 ml (4.8 mmol) ethyl vinyl ether were added. After 6 hours at 40° C. the reaction the mixture was hydrolyzed with 3 ml of a saturated aqueous $NH_4Cl$ solution. After extraction with 50 ml diethyl ether the combined organic phases were washed ($H_2O$), dried ($Na_2SO_4$) and the solvent was evaporated. Flash chromatography, using $SiO_2$ (105 g) and n-pentane/diethyl ether=95:5 as eluent, afforded 215 mg (yield: 19%) of (26).

$^1$H-NMR: 6.33 (dd, J=13.3, J=6.1, 1H), 4.37 (d, J=12.8, 1H), 4.03 (d, J=6.2, 1H) 2.45 (ddd, J=13.3, J=4.1, J=2.1, 1H), 2.35 (d, J=8.2, 1H), 2.25-2.17 (m, 1H), 2.13-2.02 (m, 1H), 1.99-1.91 (m, 2H), 1.90-1.73 (m, 2H), 1.71-1.24 (m, 15H), 1.09-1.03 (m, 1H), 0.99 (d, J=6.7, 3H).

$^{13}$C-NMR: 209.4, 144.4, 92.4, 86.0, 56.2, 49.5, 41.2, 34.3, 27.5, 27.0, 26.6, 26.1, 25.8, 25.0, 24.9, 22.0, 21.9, 19.6.

Example 10

Preparation of (1RS,11RS,14RS)-1-butoxyethoxy-14-methylbicyclo[9.4.0]-pentadecan-12-one (27)

A mixture of 2 g (7.9 mmol) of (16) and 0.84 ml (8.7 mmol) buthyl vinyl ether in 2 ml THF was stirred at room temperature in the presence of 20 µl (0.32 mmol) trifluoroacetic acid for 1 day. Flash chromatography of the reaction mixture, using $SiO_2$ (80 g) and pentane/EtOAc=9:1 as eluent, afforded 2.3 g (82%) of (27) as a ~1:1 mixture of diastereomers.

First Isomer:
$^1$H-NMR: 4.88 (q, J=5.1, 1H), 3.48 (dt, J=9.3, J=6.6, 1H), 3.35 (dt, J=8.9, J=6.7, 1H), 2.43-2.34 (m, 2H), 2.25-2.16 (m, 1H), 2.04-1.81 (m, 5H), 1.68-1.34 (m, 16H), 1.32-1.22 (m, 3H), 1.17 (d, J=5.6, 3H), 1.09-1.02 (m, 1H), 0.99 (d, J 6.7, 3H), 0.93 (t, J=7.2, 3H).

$^{13}$C-NMR: 210.3, 92.1, 85.2, 60.7, 56.4, 49.7, 40.5, 35.0, 32.2, 28.3, 27.3, 26.4, 26.2, 25.9, 25.1 (2C), 22.5, 22.1, 20.8, 19.7, 19.6, 14.0.

Second Isomer:
$^1$H-NMR: 4.94 (q, J=5.1, 1H), 3.37-3.33 (m, 2H), 2.44-2.32 (m, 2H), 2.16-2.07 (m, 1H), 1.95-1.86 (m, 2H), 1.82-1.73 (m, 2H), 1.68-1.26 (m, 20H), 1.16 (d, J=5.1, 3H), 1.05-1.00 (m, 1H), 0.98 (d, J=6.1, 3H), 0.92 (t, J=7.2, 3H).

$^{13}$C-NMR: 210.7, 93.7, 84.7, 62.6, 56.6, 49.8, 43.3, 33.7, 32.2, 28.2, 27.2, 26.5, 26.0, 25.8, 25.2, 25.1, 22.3, 22.1, 20.6, 19.8, 19.5, 13.9.

Example 11

Preparation of (1RS,11RS,14RS)-14-methyl-12-oxobicyclo[9.4.0]-pentadecan-1-yl acetate (28)

2.5 g (10 mmol) of (16) were added to a mixture of 4 g (40 mmol) $Ac_2O$ and 95 mg (0.5 mmol) $pTsOH.H_2O$ at 0° C. After stirring for 1 hour at 0° C. the mixture was warmed up to room temperature. After 60 minutes, the reaction mixture was poured into 10 g of ice and 10 ml of a saturated aqueous $NH_4Cl$ solution. After extraction with 150 ml diethyl ether the combined organic phases were washed (saturated aqueous $NaHCO_3$ and NaCl solution), dried ($Na_2SO_4$) and 1 ml $Et_3N$ were added. The solvent was evaporated. Flash chromatography, using $SiO_2$ (300 g) and n-pentane/EtOAc/$Et_3N$=95/4/1 as eluent, afforded 1.31 g (4.4 mmol, yield: 44%) of (28).

$^1$H-NMR: 2.89 (ddd, J=13.8, J=3.0, J=3.0, 1H), 2.57-2.50 (m, 1H), 2.46 (ddd, J=13.3, J=3.6, J=2.0, 1H), 2.33 (d, J=7.6, 1H), 2.22-2.13 (m, 1H), 1.98 (t, J=13.3, 1H), 1.91 (s, 3H), 1.89-1.80 (m 2H), 1.71-1.27 (m, 16H), 1.01 (d, J=6.7, 3H).

$^{13}$C-NMR: 209.3, 170.1, 91.0, 57.0, 49.6, 40.1, 33.4, 28.5, 27.0, 26.5, 26.0, 25.8, 25.1, 24.8, 22.1, 22.0, 21.7, 19.6.

Example 12

Preparation of optically active 14-methyl-bicyclo[9.4.0]-pentadec-1(11)-en-12-one (24)

General Procedure

In the reaction vessel, under inert atmosphere, were introduced 0.25 mmol of (18), (26), (27), (28) or (19), 1 ml of dry THF, and the Na or K salt of the amino alcohol (7), (6) or (8), according to Table 1. The total amount of THF present was calculated in order to keep the concentration of (18), (26), (27), (28) or (19) between 0.2 and 0.3 mol/l at the beginning of the reaction.

The reaction mixture was stirred at the temperature, according to Table 1, and followed by GC. To stop the reaction the mixture was hydrolyzed with 3 ml of a saturated $NH_4Cl$ solution. After extraction of the aqueous layer with diethyl ether the organic layer was dried over $MgSO_4$ and filtered. The solvent was removed under vacuum and the residue was purified by flash chromatography to yield in the desired product, i.e. (S)-14-methyl-bicyclo[9.4.0]pentadec-1(11)-en-12-one or (R)-14-methyl-bicyclo[9.4.0]pentadec-1(11)-en-12-one or an optically active mixture of said stereoisomers depending on the configuration of the alkoxide.

$^1$H-NMR: 1.04 (d, J=6.1, 3H), 1.18-1.46 (m, 10H), 1.50-1.75 (m, 4H), 1.97-2.15 (m, 3H), 2.30-2.40 (m, 3H), 2.41-2.56 (m, 3H).

$^{13}$C-NMR: 21.3, 23.5, 24.6, 25.1, 25.3, 25.5, 26.0, 26.2, 26.6, 29.7, 32.3, 38.3, 46.7, 136.3, 158.2, 199.7.

The results obtained are shown in Table 1.

TABLE 1

Yields and e.e. of the final product as a function of the alkoxide used

| Starting compound | Alkoxide[1] | Eq.[3] | t[4] | T | Yield[5] | e.e[6] |
|---|---|---|---|---|---|---|
| (18) | Na salt of (7) | 2 | 2 | −50 | 36 | 87% ee (S) |
| (18) | Na salt of (7) | 2 | 3 | −50 | 40 | 86% ee (S) |
| (18) | Na salt of (7) | 0.5 | 0.5 | −20 | 30 | 78% ee (S) |
| (18) | Na salt of (7) | 0.5 | 1 | −20 | 42 | 71% ee (S) |
| (18) | Na salt of (7) | 0.2 | 2 | −15 | 31 | 71% ee (S) |
| (18) | Na salt of (7) | 0.1[7] | 3 | 0 | 42 | 56% ee (S) |
| (19) | Na salt of (7) | 2 | 0.5 | 0 | 20 | 75% ee (S) |
| (19) | Na salt of (7) | 2 | 2 | 0 | 40 | 60% ee (S) |
| (18) | Na salt of (8) | 2 | 0.25 | −10 | 25 | 78% ee (S) |
| (18) | Na salt of (6) | 2 | 1 | −25 | 12 | 54% ee (R) |
| (19) | K salt of (7) | 0.1[8] | 1 | −30 | 37 | 48% ee (S) |
| (26) | Na salt of (7) | 2 | 0.5 | −60 | 53 | 62% ee (S) |
| (27) | Na salt of (7) | 2 | 2 | −50 | 35 | 86% ee (S) |
| (28) | Na salt of (7) | 2 | 3 | −78 | 17 | 50% ee (S) |

[1] see description
[3] number of molar equivalent of alkoxide introduced, relative to the starting material
[4] duration of the reaction in hours
[5] determined by GC
[6] determined by reacting the final product with an excess of $LiAlH_4$ in dry THF. After hydrolysis, filtration and extraction with $Et_2O$, the allyl alcohol obtained was analyzed by GC with a chiral column (CHIRASIL DEX CB) to determine the enantiomeric excess of the resulting allyl alcohol.
[7] reaction was performed in the presence of 2 eq NaH
[8] reaction was performed in the presence of 2 eq KH and 0.05 eq MeOH When the reaction was done with (18), (19) or (27), the reaction mixture, obtained above after a conversion of about 40%, can be alternatively treated 10 minutes with a mixture of 0.4 ml $H_2O$ and 0.4 ml of an aqueous 1N HCl solution. After extraction of the aqueous layer with diethyl ether the organic layer was washed (saturated aqueous $NaHCO_3$ solution, $H_2O$), dried over $MgSO_4$ and filtered. The solvent was removed under vacuum and the residue was purified by flash chromatography to yield in the desired product, i.e. (1R,11S,14R)-1-hydroxy-14-methyl-bicyclo[9.4.0]pentadecan-12-one or (1S,11R,14S)-1-hydroxy-14-methyl-bicyclo[9.4.0]pentadecan-12-one or an optically active mixture of said stereoisomers depending on the configuration of the alkoxide and (S)-14-methyl-bicyclo[9.4.0]pentadec-1(11)-en-12-one or (R)-14-methyl-bicyclo[9.4.0]pentadec-1(11)-en-12-one or an optically active mixture of said stereoisomers depending on the configuration of the alkoxide.

Example 13

Preparation of optically active 3-butyl-5-methyl-2-propyl-2-cyclohexen-1-one (25)

General Procedure

In the reaction vessel, under inert atmosphere, were introduced 0.5 mmol of (22) or (23), 2 ml of dry THF, and the Na or K salt of the amino alcohol (7), according to Table 2. The total amount of THF present was calculated in order to keep the concentration of the (22) or (23) between 0.2 and 0.3 mol/L at the beginning of the reaction. The reaction mixture was stirred at the temperature, according to Table 2, and followed by GC. To stop the reaction the mixture was hydrolyzed with 3 ml of a saturated $NH_4Cl$ solution. After extraction of the aqueous layer with diethyl ether the organic layer was dried over $MgSO_4$ and filtered. The solvent was removed under vacuum and the residue was purified by flash chromatography to yield in the desired product, i.e. (S)-3-butyl-5-methyl-2-propyl-2-cyclohexen-1-one or (R)-3-butyl-5-methyl-2-propyl-2-cyclohexen-1-one or an optically active mixture of said stereoisomers depending on the configuration of the alkoxide.

$^1$H-NMR: 0.89 (t, J=7.7, 3H), 0.94 (t, J=7.2, 3H), 1.02 (d, J=6.2, 3H), 1.27-1.49 (m, 6H), 1.98-2.13 (m, 3H), 2.17-2.29 (m, 4H), 2.33 (d, J=15.3, 1H), 2.45 (d, J=14.4, 1H).

$^{13}$C-NMR: 14.0, 14.3, 21.2, 22.9, 23.0, 27.0, 29.8, 30.1, 34.7, 39.1, 46.2, 135.0, 158.3, 199.5.

The results obtained are shown in Table 2.

TABLE 2

Yields and e.e. of the final product as a function of the alkoxide used

| Starting compound | Alkoxide[1] | Eq.[3] | t[4] | T | Yield[5] | e.e[6] |
|---|---|---|---|---|---|---|
| (22) | Na salt of (7) | 2 | 1.5 | −45 | 30 | 54% ee (S) |
| (23) | Na salt of (7) | 2 | 0.5 | 0 | 18 | 51% ee (S) |

[1])see description
[3])number of molar equivalent of alkoxide introduced, relative to the starting material
[4])duration of the reaction in hours
[5])determined by GC
[6])determined by reacting the final product with an excess of LiAlH$_4$ in dry THF. After hydrolysis, filtration and extraction with Et$_2$O, the allyl alcohol obtained was analyzed by GC with a chiral column (CHIRASIL DEX CB) to determine the enantiomeric excess of the resulting allyl alcohol.

Example 14

Preparation of (IRS,10RS,13RS)-1-hydroxy-13-methylbicyclo[8.4.0]tetradecan-11-one (30)

A solution of 3-methyl-1,5-cyclotetradecanedione 29 (500 mg, 2.1 mmol) in CH$_2$Cl$_2$ (4 ml) was treated at 22-24° C. with a solution of ZrCl$_3$OPr (36% in AcOBu) (1.79 g, 3.86 mmol). After 15 minutes the solution was treated at −10° C. with NBu$_3$ (0.68 g, 0.88 ml, 3.68 mmol). After 70 minutes, the reaction mixture was poured into 5 ml water and 7 ml of a aqueous 2 NHC1 solution were added. After extraction with 25 ml diethyl ether the combined organic phases were washed (saturated aqueous NaHCO$_3$ solution, H$_2$O), dried (Na$_2$SO$_4$) and the solvent was evaporated (crude 531 mg). Flash chromatography, using SiO$_2$ (25 g) and n-pentane/diethyl ether=6:4 as eluent, afforded 364 mg (yield: 73%) of (30).

$^1$H-NMR: 2.59 (d, J=7.7, 1H), 2.46-2.41 (m, 1H), 2.36-2.15 (m, 2H), 1.98 (t, J=12.8, 2H), 1.74-1.31 (m, 17H), 1.02 (d, J=6.6, 3H).

$^{13}$C-NMR: 210.6, 79.7, 53.4, 49.8, 44.9, 38.4, 28.7, 27.6, 27.1, 25.9, 24.6, 24.0, 22.3, 22.1, 18.4.

Example 15

Preparation of (1RS,10RS,13RS)-1-(1-ethoxy-ethoxy)-13-methylbicyclo[8.4.0]tetradecan-11-one (31)

A mixture of 119 mg (0.5 mmol) of (30) and 384 μl (4 mmol) ethyl vinyl ether was stirred at 25° C. in the presence of 25 mg (0.1 mmol) pyridinium p-toluenesulfonate (PPTS) for 2 hours (94% conversion). Flash chromatography of the reaction mixture, using SiO$_2$ (14 g) and n-pentane/diethyl ether=95:5 as eluent, afforded 105 mg (61%) of (31) as a ~1:1 mixture of diastereomers.

First Isomer:
$^1$H-NMR (CD$_2$Cl$_2$): 4.86 (q, J=5.6, 1H), 3.54-3.39 (m, 2H), 2.49 (d, J=7.7, 2H), 2.36-2.32 (m, 1H), 2.19-2.11 (m, 1H), 1.86-1.19 (m, 18H), 1.15 (d, J=6.0, 3H), 1.12 (t, J=7.1, 3H), 0.99 (d, J=6.2, 3H).

$^{13}$C-NMR (CD$_2$Cl$_2$): 209.9, 92.6, 85.8, 57.2, 54.2, 49.9, 41.0, 33.8, 28.8, 28.1, 28.0, 27.7, 25.1, 25.0, 22.7, 22.2, 21.2, 19.4, 15.7.

Second Isomer:
$^1$H-NMR (CD$_2$Cl$_2$): 4.91 (q, J=5.1, 1H), 3.37 (qd, J=7.2, J=1.5, 2H), 2.48 (d, J=7.7, 1H), 2.45-2.37 (m, 1H), 2.34-2.31 (m, 1H), 2.14-2.07 (m, 1H), 1.97-1.84 (m, 2H), 1.84-1.81 (m, 2H), 1.71-1.41 (m, 12H), 1.31-1.19 (m, 2H), 1.13 (d, J=5.1, 3H), 1.10 (t, J=6.7, 3H), 0.97 (d, J=6.6, 3H).

$^{13}$C-NMR (CD$_2$Cl$_2$): 210.3, 94.0, 85.4, 59.1, 54.5, 50.0, 43.3, 32.6, 28.6, 28.1, 28.0, 27.6, 25.0 (2C), 22.5, 22.2, 21.2, 19.5, 15.7.

Example 16

Preparation of optical active 13-methyl-bicyclo[8.4.0]tetradec-1(10)-en-11-one (32)

General Procedure

In the reaction vessel, under inert atmosphere, were introduced 0.25 mmol of (31), 1 ml of dry THF, and the Na salt of the amino alcohol (7), according to Table 3. The total amount of THF present was calculated in order to keep the concentration of (31) between 0.2 and 0.3 mol/l at the beginning of the reaction.

The reaction mixture was stirred at the temperature, according to Table 3, and followed by GC. To stop the reaction the mixture was hydrolyzed with 3 ml of a saturated NH$_4$Cl solution. After extraction of the aqueous layer with diethyl ether the organic layer was dried over MgSO$_4$ and filtered. The solvent was removed under vacuum and the residue was purified by flash chromatography to yield in the desired product, i.e. (S)-13-methyl-bicyclo[8.4.0]tetradec-1 (10)-en-11-one or (R)-13-methyl-bicyclo[8.4.0]tetradec-1 (10)-en-11-one or an optically active mixture of said stereoisomers depending on the configuration of the alkoxide.

$^1$H-NMR: 2.54-2.46 (m, 4H), 2.34 (d, J=16.9, 1H), 2.37-1.96 (m, 3H), 1.76-1.58 (m, 4H), 1.47-1.16 (m, 9H), 1.04 (d, J=6.1, 3H).

$^{13}$C-NMR: 199.5, 158.4, 134.8, 46.7, 38.0, 32.7, 29.7, 27.1, 25.8, 25.7, 25.5, 23.4, 21.4, 21.4, 21.1.

The results obtained are shown in Table 3.

TABLE 3

Yields and e.e. of the final product as a function of the alkoxide used

| Starting compound | Alkoxide[1] | Eq.[3] | t[4] | T | Yield[5] | e.e[6] |
|---|---|---|---|---|---|---|
| (31) | Na salt of (7) | 2 | 1 | −30 | 20 | 71% ee (S) |

[1])see description
[3])number of molar equivalent of alkoxide introduced, relative to the starting material
[4])duration of the reaction in hours
[5])determined by GC
[6])determined by reacting the final product with an excess of LiAlH$_4$ in dry THF. After hydrolysis, filtration and extraction with Et$_2$O, the allyl alcohol obtained was analyzed by GC with a chiral column (CHIRASIL DEX CB) to determine the enantiomeric excess of the resulting allyl alcohol.

Example 17

Preparation of (1RS,12RS,15RS)-1-hydroxy-15-methyl-bicyclo[10.4.0]hexadecan-13-one (34)

A solution of 3-methyl-1,5-cyclohexadecanedione (33) (1 g, 3.76 mmol) in CH$_2$Cl$_2$ (6 ml) was treated at 22-24° with a solution of ZrCl$_3$OPr (36% in AcOBu) (3 g, 5.0 mmol). After 15 minutes the solution was treated at −10° C. with NBu$_3$ (1.15 g, 1.48 ml, 6.2 mmol). After 60 minutes, the reaction mixture was poured into 15 ml water and 15 ml of a 2 N HCl solution were added. After extraction with 50 ml diethyl ether the combined organic phases were washed (saturated aqueous $NaHCO_3$ solution, $H_2O$), dried ($Na_2SO_4$) and the solvent was evaporated (crude 1.0 g). Flash chromatography, using $SiO_2$ (100 g) and n-pentane/diethyl ether=6:4 as eluent, afforded 898 mg (yield: 90%) of (34).

$^1$H-NMR: 2.43-2.37 (m, 2H), 2.32-2.21 (m, 1H), 2.00-1.85 (m, 3H), 1.69-1.66 (m, 2H), 1.55-1.18 (m, 19H), 1.01 (d, J=6.7, 3H).

$^{13}$C-NMR: 211.2, 79.4, 53.1, 50.3, 45.0, 39.1, 28.9, 26.6, 26.1, 26.0, 23.2, 22.9, 22.8, 22.1, 22.0, 21.2, 17.9.

Example 18

Preparation of (1RS,12RS,15RS)-1-(ethoxyethoxy)-15-methyl-bicyclo[10.4.0]hexadecan-13-one (35)

A mixture of 133 mg (0.5 mmol) of (34) and 67 µl (0.7 mmol) ethyl vinyl ether in 0.4 ml $CH_2Cl_2$ was stirred at 40° C. in the presence of 63 mg (0.25 mmol) pyridinium p-toluenesulfonate (PPTS) for 3 hours (57% conversion). Flash chromatography of the reaction mixture, using $SiO_2$ (14 g) and n-pentane/diethyl ether=9:1 as eluent, afforded 42 mg (25%) of (35) as a ~1:1 mixture of diastereomers and 72 mg (0.27 mmol) of the starting material (34).

First Isomer:
$^1$H-NMR ($CD_2Cl_2$): 4.87 (q, J=5.6, 1H), 3.54-3.38 (m, 2H), 2.34-2.31 (m, 2H), 1.98-1.87 (m, 4H), 1.76-1.69 (m, 1H), 1.55-1.21 (m, 19H), 1.15 (d, J=5.6, 3H), 1.12 (t, J=7.2, 3H), 0.99 (d, J=6.1, 3H).

$^{13}$C-NMR ($CD_2Cl_2$): 210.4, 92.5, 85.3, 57.2, 54.2, 50.5, 41.0, 34.8, 29.0, 27.6, 26.8, 26.5, 23.7, 23.4, 23.4, 22.7, 22.2, 21.8, 21.2, 18.7, 15.7.

Second Isomer:
$^1$H-NMR ($CD_2Cl_2$): 4.91 (q, J=5.1, 1H), 3.46-3.35 (m, 2H), 2.42-2.28 (m, 3H), 1.96-1.19 (m, 23H), 1.14 (d, J=5.1, 3H), 1.12 (t, J=7.2, 3H), 0.98 (d, J=6.7, 3H).

$^{13}$C-NMR ($CD_2Cl_2$) 210.8, 93.9, 85.0, 58.9, 54.3, 50.6, 43.3, 33.3, 28.8, 27.5, 26.7, 26.4, 23.7, 23.4 (2C), 22.7, 22.2, 21.8, 21.0, 18.8, 15.7.

Example 19

Preparation of optical active 15-methylbicyclo[10.4.0]hexadec-1(12)-en-13-one (36)

General Procedure

In the reaction vessel, under inert atmosphere, were introduced 0.25 mmol of (35), 1 ml of dry THF, and the Na salt of the amino alcohol (7), according to Table 4. The total amount of THF present was calculated in order to keep the concentration of (35) between 0.2 and 0.3 mol/l at the beginning of the reaction.

The reaction mixture was stirred at the temperature, according to Table 4, and followed by GC. To stop the reaction the mixture was hydrolyzed with 3 ml of a saturated $NH_4Cl$ solution. After extraction of the aqueous layer with diethyl ether the organic layer was dried over $MgSO_4$ and filtered. The solvent was removed under vacuum and the residue was purified by flash chromatography to yield in the desired product, i.e. (S)-15-methyl-bicyclo[10.4.0]hexadec-1(12)-en-13-one or (R)-15-methyl-bicyclo[10.4.0]hexadec-1(12)-en-13-one or an optically active mixture of said stereoisomers depending on the configuration of the alkoxide.

$^1$H-NMR: 2.47-2.20 (m, 6H), 2.14-1.99 (m, 3H), 1.69-1.37 (m, 14H), 1.27-1.21 (m, 2H), 1.02 (d, J=5.1, 3H).

$^{13}$C-NMR: 199.8, 158.5, 135.1, 46.5, 38.9, 31.9, 29.8, 27.0, 26.3, 25.7, 25.5, 25.1, 24.2, 23.0, 22.8, 22.0, 21.2.

The results obtained are shown in Table 4.

TABLE 4

Yields and e.e. of the final product as a function of the alkoxide used

| Starting compound | Alkoxide[1] | Eq.[3] | t[4] | T | Yield[5] | e.e[6] |
|---|---|---|---|---|---|---|
| (35) | Na salt of (7) | 2 | 2 | −15 | 36 | 80% ee (S) |

[1]see description
[3]number of molar equivalent of alkoxide introduced, relative to the starting material
[4]duration of the reaction in hours
[5]determined by GC
[6]determined by reacting the final product with an excess of $LiAlH_4$ in dry THF. After hydrolysis, filtration and extraction with $Et_2O$, the allyl alcohol obtained was analyzed by GC with a chiral column (CHIRASIL DEX CB) to determine the enantiomeric excess of the resulting allyl alcohol.

The invention claimed is:

1. A compound of formula

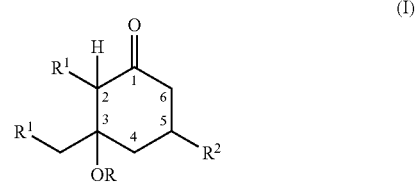

wherein
$R^1$, taken separately, are identical and represent an achiral $Cl_{1-10}$ linear, branched or cyclic alkyl or alkenyl group optionally substituted, or alternatively said two $R^1$, taken together, represent a linear $C_3$-$C_{10}$ alkanediyl or alkenediyl group optionally substituted;
$R^2$ represents an achiral $C_{1-7}$ linear, branched or cyclic alkyl or alkenyl group optionally substituted or a phenyl or benzyl group optionally substituted; and
R represents:
a hydrogen atom,
a group of formula Si $(R^3)_3$, where $R^3$ representing a $C_{1-7}$ linear, branched or cyclic alkyl or alkenyl group or a phenyl group optionally substituted,
a $C_1$-$C_{10}$ sulfonyl group, or
a $C_1$-$C_{10}$ hydrocarbon group optionally comprising up to four heteroatoms selected from the group consisting of oxygen, nitrogen, silicium or sulfur, provided that said heteroatom is not directly bonded to the oxygen atom bearing said R group;
and further with the substituents of R, $R^1$ and $R^2$ being one or two $C_{1-5}$ alkyl, alkoxy or cycloalkyl group.

2. A compound according to claim 1, wherein the R group represents a hydrogen atom, a $C_{1-6}$ linear, branched or cyclic alkyl, alkenyl or acyl group optionally substituted, an optionally substituted benzyl group, a $C_1$-$C_{10}$ sulfonyl group, a group of formula —$CH(R^a)OCH_2R^a$, $R^a$ representing a hydrogen atom or a $C_{1-5}$ alkyl group or, taken together, representing a $C_1$-$C_5$ group, or a group of formula Si $(R^3)_3$, $R^3$ representing a $C_{1-7}$ linear, branched or cyclic alkyl or alkenyl group or a phenyl group optionally substituted.

3. A compound according to claim 1, having the formula

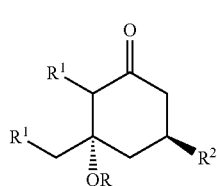

(II)

wherein the groups OR and $R^2$ are in a relative configuration trans.

4. A compound according to claim 1, in the form of an optically active compound of formula:

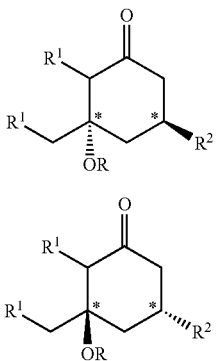

(III)

(III')

wherein the asterisks designate that the configuration of the carbon is absolute such that compound (III) or (III') is in an optically active form.

5. A compound according to claim 1, wherein:
the $R^1$ groups, taken separately, are identical and represent an achiral $C_{1-5}$ linear, branched or cyclic alkyl or alkenyl group or alternatively said two $R^1$, taken together, represent a linear $C_3$-$C_{10}$ alkanediyl or alkenediyl group;

$R^2$ represents an achiral $C_{15}$ linear or branched alkyl or alkenyl group or a phenyl group; and R represents a hydrogen atom, a $C_{1-5}$ linear, branched or cyclic alkyl or alkenyl group optionally substituted, a benzyl group, a group of formula —CH($R^a$)OCH$_2R^a$, $R^a$ representing a hydrogen atom or a methyl, ethyl or n-propyl group or, taken together, representing a $C_3$-$C_4$ group, or a group of formula Si $(R^3)_3$, $R^3$ representing a $C_{1-5}$ linear, branched alkyl group or a phenyl group.

6. As a compound according to claim 1:
(−)-(1R,11S,14R)-1-Hydroxy-14-methyl-bicyclo[9.4.0]pentadecan-12-one,
(−)-(1R,11R,14R)-1-Hydroxy-14-methyl-bicyclo[9.4.0]pentadecan-12-one,
(1RS,11RS,14RS)-1-Hydroxy-14-methyl-bicyclo[9.4.0]pentadecan-12-one,
(1RS,11RS,14RS)-1-ethoxyethoxy-14-methylbicyclo[9.4.0]pentadecan-12-one, or
(1RS,11RS,14RS)-14-methyl-1-trimethylsilyloxybicyclo[9.4.0]pentadecan-12-one.

7. A process for the preparation of an optically active compound of formula:

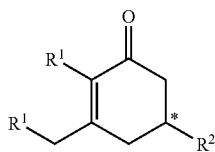

(V)

which comprises:
treating a trans ketone of one of formulae (II), (III), or (III') with an optically active sodium or potassium alkoxide under conditions sufficient to produce the compound of formula V while optionally removing water:

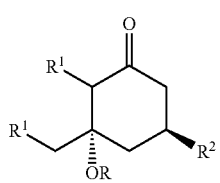

(II)

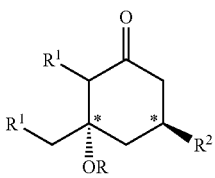

(III)

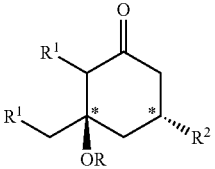

(III')

wherein each asterisk designates that the configuration of the carbon is absolute such that the compound is in an optically active form and $R^1 R^2$ and R are as defined in claim 1 provided that R is not a hydrogen atom.

8. A process according to claim 7, wherein the optically active sodium or potassium alkoxide is
a) a sodium or potassium salt of a $C_4$-$C_{18}$ optically active mono alcohol of formula

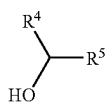

(A)

wherein $R^5$ represents a $C_{1-4}$ alkyl group or an optionally substituted phenyl group and $R^4$ represents a $C_{1-4}$ alkyl group or a C($R^{5'})_2$(OR$^{4'}$) group, $R^{5'}$ representing a hydrogen atom or a $R^5$ group and $R^{4'}$ representing a $C_{1-6}$ alkyl group or a $C_{3-9}$ trialkyl silyl or a triphenyl silyl group; or
of formula $R^4$—OH, wherein $R^{4''}$ represents a $C_{7-12}$ chiral hydrocarbon group;

b) a sodium or potassium salt of a $C_3$-$C_{18}$ optically active 1,2-diol of formula

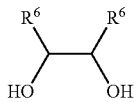
(B)

wherein $R^6$ represents an optionally substituted phenyl group, a $C_{1-6}$ alkyl group or a $COOR^7$ group, $R^7$ representing a $C_{1-4}$ alkyl group;

a $C_4$-$C_{18}$ optically active 1,3-diol of formula

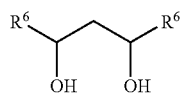
(C)

wherein $R^6$ has the meaning indicated above;

a $C_5$-$C_{35}$ optically active 1,4-diol containing a moiety of formula

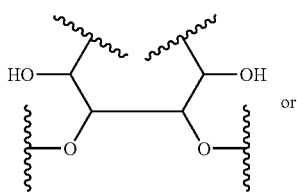
(D)

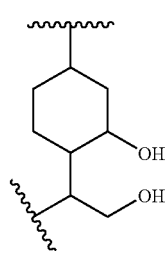
(D')

or a sodium or potassium salt of an optically active diol of formula

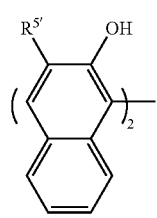
(D'')

wherein $R^{5'}$ has the meaning indicated above;

c) a sodium or potassium salt of a $C_4$-$C_２５$ optically active alcohol containing a nitrogen in the β position of formula

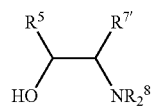
(E)

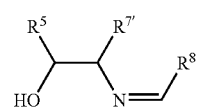
(E')

wherein $R^5$ has the meaning indicated above, $R^{7'}$ represents a $R^4$ or $R^5$ group as defined above and $R^8$ represents an optionally substituted phenyl group, a $C_{1-9}$ alkyl or alkylbenzene group a $SiR^{7'}_3$ group or a $R^{7'}CO$ group; optionally $R^5$ and $R^{7'}$ can be bonded together to form a $C_{5-10}$ ring or $R^{7'}$ and a $R^8$ can be bonded together to form a $C_{4-5}$ heterocycle, or the two $R^8$ can be bonded together to form a $C_{2-5}$ heterocycle;

d) a sodium or potassium salt of an optically active iminoalcohol of formula

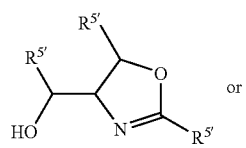
(F)

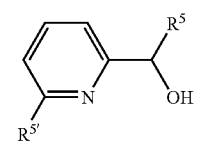
(F')

wherein $R^5$ and $R^{5'}$ have the meaning indicated above;

e) a sodium or potassium salt of a $C_{15-38}$ compound having two or three groups derived from an optically active alkoxide mentioned under a), b), c) or d); or f) a sodium or potassium salt of an optically active alkoxide mentioned under e) and which is supported on an insoluble material such as silica, Merrifield resins, gold or polystyrenes;

the substituents of phenyl groups being $R^b$, $SR^b$, $NO_2$ or $OR^b$ groups or halogen atoms, wherein $R^b$ stands for a $C_{1-4}$ alkyl group.

9. A process according to claim 8, wherein the optically active sodium or potassium alkoxide is a sodium or potassium salt of a $C_4$-$C_{25}$ optically active alcohol containing a nitrogen in the β position of formula

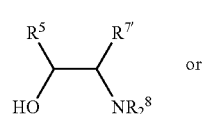
(E)

or

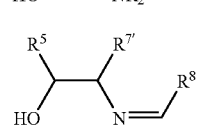
(E')

wherein
- $R^5$ represents a $C_{1-4}$ alkyl group or an optionally substituted phenyl group, $R^{7'}$ represents a $R^4$ or $R^{5'}$ group where $R^4$ represents a $C_{1-4}$ alkyl group or a $C(R^{5'})_2$ (OR$^{4'}$) group,
- $R^{5'}$ represents a hydrogen atom or a $R^5$ group and $R^{4'}$ representing a $C_{1-6}$ alkyl group or a $C_{3-9}$ trialkyl silyl or a triphenyl silyl group, and
- $R^8$ represents an optionally substituted phenyl group, a $C_{1-9}$ alkyl or alkylbenzene group a $SiR^{7'}_3$ group or a $R^{7'}CO$ group; optionally $R^5$ and $R^{7'}$ can be bonded together to form a $C_{5-10}$ ring or $R^{7'}$ and a $R^8$ can be bonded together to form a $C_{4-5}$ heterocycle, or the two $R^8$ can be bonded together to form a $C_{2-5}$ heterocycle.

10. A process for the preparation of a compound of formula

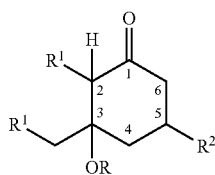

(I)

wherein
- $R^1$, taken separately, are identical and represent an achiral $C_{1-10}$ linear, branched or cyclic alkyl or alkenyl group optionally substituted, or alternatively said two $R^1$, taken together, represent a linear $C_3$-$C_{10}$ alkanediyl or alkenediyl group optionally substituted;
- $R^2$ represents an achiral $C_{1-7}$ linear, branched or cyclic alkyl or alkenyl group optionally substituted or a phenyl or benzyl group optionally substituted; and
- R represents:
  - a hydrogen atom,
  - a group of formula Si $(R^3)_3$, $R^3$ representing a $C_{1-7}$ linear, branched or cyclic alkyl or alkenyl group or a phenyl group optionally substituted,
  - a $C_1$-$C_{10}$ sulfonyl group, or
  - a $C_1$-$C_{10}$ hydrocarbon group optionally comprising up to four heteroatoms selected from the group consisting of oxygen, nitrogen, silicium or sulfur, provided that said heteroatom is not directly bonded to the oxygen atom bearing said R group;

the substituents of R, $R^1$ and $R^2$ being one or two $C_{1-5}$ alkyl, alkoxy or cycloalkyl group which comprises:

a) treating an achiral di-ketone of formula

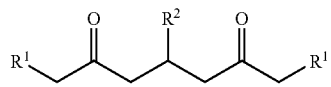

(VI)

wherein $R^1$, taken separately, are identical and represent an achiral $C_{1-10}$ linear, branched or cyclic alkyl or alkenyl group optionally substituted, or alternatively said two $R^1$, taken together, represent a linear $C_3$-$C_{10}$ alkanediyl or alkenediyl group optionally substituted; and $R^2$ represents an achiral $C_{1-7}$ linear, branched or cyclic alkyl or alkenyl group optionally substituted or a phenyl or benzyl group optionally substituted, with a $C_3$-$C_{24}$ amine or diamine, in a racemic or optically active form; and in the presence of a complex obtainable by admixing TiCl$_4$ or ZrCl$_4$ with an equimolar amount of an alcohol $R^bOH$, $R^b$ representing a $C_1$-$C_5$ alkoxy group, or of a chiral ligand selected from the group consisting of an optically active alcohol of formula (E), (E'), (F) or (F'), as defined in claim 8, and an optically active alcohol of formula

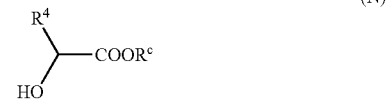

(N)

wherein $R^4$ has the meaning indicated above and $R^c$ represents a $C_{1-4}$ alkyl group, to form a reaction medium;

b) hydrolyzing the reaction medium of a) to obtain a compound of formula (I) wherein R is a hydrogen atom; and c) converting the compound obtained in b) by treating it with an appropriate reagent, into a compound of formula (I) wherein R is not a hydrogen atom.

11. A process according to claim 10, wherein the appropriate reagent is a compound of formula Si $(R^3)_3X$, $R^3$ representing a $C_1$-$C_4$ alkyl group or a phenyl group and X representing a chloride atom or a $CF_3SO_3$ group or is compound of formula XCH($R^a$)OCH$_2R^a$, or of formula HR$^{a'}$C=CHOCH$_2R^a$, are those wherein $R^a$ or $R^a$, taken separately, represents a hydrogen atom or a methyl, ethyl, propyl or isopropyl group, or $R^a$ and $R^a$, taken together, represents a CH$_2$CH$_2$ or CH$_2$CH$_2$CH$_2$ group.

12. A process for the preparation of an optically active compound of formula:

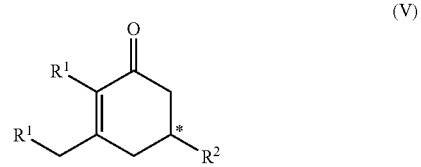

(V)

wherein the asterisk designates that the configuration of the carbon is absolute such that compound (V) is in an optically active form, which process comprises treating an optically active trans ketone of formula (III) or (III')

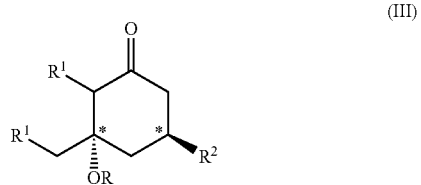

(III)

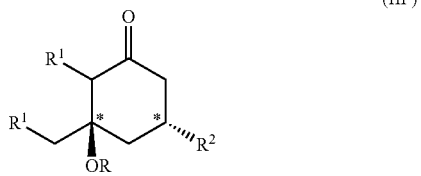

(III')

wherein $R^1$ and $R^2$ have the meaning indicated in claim 1 and R is hydrogen, with a $C_1$-$C_8$ sulfonyl chloride in the presence of a tertiary $C_3$-$C_{24}$ amine under conditions sufficient to produce the compound of formula V.

* * * * *

UNITED STATES PATENT AND TRADEMARK OFFICE
CERTIFICATE OF CORRECTION

PATENT NO.       : 7,470,820 B2
APPLICATION NO.  : 11/916258
DATED            : December 30, 2008
INVENTOR(S)      : Knopff et al.

It is certified that error appears in the above-identified patent and that said Letters Patent is hereby corrected as shown below:

Column 25:
Line 45, after "$R^2$ represents an achiral", change "$C_{15}$" to -- $C_{1-5}$ --.

Column 26:
Line 65, change "$R^4$—OH," to -- $R^{4'}$—OH --.

Column 28:
Line 1, change "$C_4$-$C_2$S" to -- $C_4$-$C_{25}$ --.
Line 9, (formula (E)), change "$NR_2^8$" to -- $NR^8_2$ --.
Line 16, change "$R^5$" to -- $R^{5'}$ --.
Line 60, (formula (E)), change "$NR_2^8$" to -- $NR^8_2$ --.

Column 29:
Line 3, after "tuted phenyl group," start a new paragraph with "$R^{7'}$ represents".

Column 30:
Line 25, change "$R^a$ or $R^a$," to -- $R^a$ or $R^{a'}$ --.
Line 27, change "$R^a$ or $R^a$," to -- $R^a$ or $R^{a'}$ --.

Signed and Sealed this

Twenty-fourth Day of February, 2009

JOHN DOLL
*Acting Director of the United States Patent and Trademark Office*